(12) United States Patent
Flechsenhar et al.

(10) Patent No.: US 8,133,269 B2
(45) Date of Patent: Mar. 13, 2012

(54) VASCULAR STENT

(75) Inventors: Klaus Flechsenhar, Eberbach (DE); Michael Ahlers, Eberbach (DE)

(73) Assignee: Gelita AG, Eberbach (DE)

( * ) Notice: Subject to any disclaimer, the term of this patent is extended or adjusted under 35 U.S.C. 154(b) by 0 days.

(21) Appl. No.: 12/616,274

(22) Filed: Nov. 11, 2009

(65) Prior Publication Data
US 2010/0057200 A1     Mar. 4, 2010

Related U.S. Application Data

(63) Continuation of application No. PCT/EP2008/003894, filed on May 15, 2008.

(30) Foreign Application Priority Data

May 16, 2007  (DE) .......................... 10 2007 024 256

(51) Int. Cl.
*A61F 2/82* (2006.01)

(52) U.S. Cl. ................... 623/1.46; 623/1.15; 623/1.44

(58) Field of Classification Search ........ 623/1.42–1.48; 424/93.1; 427/2.24; *A61F 02/06*
See application file for complete search history.

(56) References Cited

U.S. PATENT DOCUMENTS

| | | | |
|---|---|---|---|
| 4,747,848 A | 5/1988 | Maini | |
| 4,902,290 A | 2/1990 | Fleckenstein et al. | |
| 5,632,776 A | 5/1997 | Kurumatani et al. | |
| 5,854,382 A | 12/1998 | Loomis | |
| 6,607,714 B1 * | 8/2003 | Dupuis et al. | 424/70.1 |
| 6,976,952 B1 | 12/2005 | Maini et al. | |
| 2003/0064074 A1 * | 4/2003 | Chang et al. | 424/184.1 |
| 2004/0117007 A1 * | 6/2004 | Whitbourne et al. | 623/1.42 |
| 2004/0215338 A1 | 10/2004 | Elkins et al. | |
| 2005/0019404 A1 | 1/2005 | Sung et al. | |
| 2005/0163821 A1 | 7/2005 | Sung et al. | |
| 2005/0229264 A1 * | 10/2005 | Chang et al. | 800/8 |
| 2007/0077274 A1 | 4/2007 | Ahlers | |
| 2008/0267919 A1 | 10/2008 | Ahlers et al. | |

FOREIGN PATENT DOCUMENTS

| | | |
|---|---|---|
| DE | 35 86 941 | 4/1993 |
| DE | 103 20 773 | 12/2004 |
| DE | 103 57 281 | 7/2005 |
| DE | 698 26 882 | 11/2005 |
| DE | 10 2004 024 635 | 12/2005 |
| DE | 10 2005 054 937 | 5/2007 |
| EP | 0 237 037 | 9/1987 |

(Continued)

OTHER PUBLICATIONS

Lagerqvist, B. et al., *The New England Journal of Medicine*, 356:1009-1019 (2007).

(Continued)

*Primary Examiner* — Thomas J Sweet
*Assistant Examiner* — Jason-Dennis Stewart
(74) *Attorney, Agent, or Firm* — Leydig, Voit & Mayer, Ltd.

(57) ABSTRACT

In order to provide a vascular stent, with which the risk of restenosis is reduced without having to use anti-proliferative active substances, there is proposed a carrier of a dimensionally stable material, as well as one or more layers, which are disposed at least in sections on the carrier, of a material based on crosslinked gelatin that is resorbable under physiological conditions, wherein the adhesion between the carrier and the layer and/or between individual layers can be neutralised.

24 Claims, 7 Drawing Sheets

FOREIGN PATENT DOCUMENTS

| | | |
|---|---|---|
| EP | 1 645 907 | 4/2006 |
| JP | 2005-312584 | 11/2005 |
| WO | WO 99/08718 | 2/1999 |
| WO | WO 02/13883 | 2/2002 |
| WO | WO 03/039615 | 5/2003 |
| WO | WO 2005/077433 | 8/2005 |

OTHER PUBLICATIONS

Meier, P. et al., *Journal of American College of Cardiology*, 49(1):15-20 (2007).
Morice, Marie-Claude et al., *The New England Journal of Medicine*, 346(23):1773-1780 (2002).
Shirota, T. et al., *Biomaterials*, 24:2295-2302 (2003).

* cited by examiner 5 d 6 d 7 d 10 d 11 d 12 d

VASCULAR STENT

CROSS-REFERENCE TO RELATED APPLICATIONS

This application is a continuation of PCT/EP2008/003894, filed May 15, 2008, which claims the priority of German patent application DE 10 2007 024 256.7, filed May 16, 2007, which are each incorporated by reference.

BACKGROUND OF THE INVENTION

The present invention relates to a vascular stent, in particular a coronary stent.

BRIEF SUMMARY OF THE INVENTION

Stents are used medically as implants to keep open and/or after an occlusion (stenosis) to re-open hollow structures of organs in the body. As a rule, in this case a small tubular stent in compressed form is introduced into the relevant organ and then expanded in order to support the walls of the organ.

Stents are of particular significance for opening blood vessels, and here in particular in the region of coronary vessels (coronary stents). Stenosis or occlusion of coronary vessels as a result of the depositing of thrombi (blood clots), blood fats or calcium on the vessel walls is a frequent cause of areas of the myocardium being under-supplied with blood and hence of cardiac infarction. The stents used to prevent or eliminate such stenoses frequently comprise a small tubular lattice frame that is introduced into the relevant vessel and radially expanded by means of a balloon catheter in order to widen the vessel to an adequate size.

Such therapies involving vascular stents however regularly give rise to the problem of so-called restenosis. By this is meant a renewed narrowing of the vessel as a result of on-stent deposits and/or overgrowth of the stent with tissue, this being induced by an activation of blood platelets and clotting factors on the "foreign material" of the stent (as a rule, metal or plastics material). Restenosis often necessitates renewed treatment of the affected vessel.

For some time now drug-coated stents (drug-eluting stents, DES) have been used to avoid or reduce this problem. These stents have a coating, from which specific active substances for inhibiting the formation of tissue (for example anti-proliferatives, cytostatic drugs or immuno-suppressants) are released. Through the use of such stents the risk of restenosis of the relevant vessel is to be markedly reduced (see M. C. Morice et al., New England Journal of Medicine 2002 (346) 1773-1780).

Drug-coated stents are disclosed i.a. in the published patent application US 2005/0019404 A1.

In recent studies it was however discovered that for patients, in which after stenosis of a coronary vessel a drug-coated stent was implanted, the mortality rate is higher than for patients who were treated with an uncoated metal stent. The quantitative result of this study was that the probability of death by cardiac infarction in the period of between 6 months and 3 years after the stent implantation was 32% higher in the first-mentioned patient group than in the last-mentioned patient group (see B. Lagerqvist et al., New England Journal of Medicine 2007 (356) 1009-1019).

The object of the present invention is to provide a stent, with which the risk of restenosis is reduced without having to use anti-proliferative active substances.

This object is achieved according to the invention by a vascular stent of the type described in the introduction, comprising a carrier of a dimensionally stable material, as well as one or more layers, which are disposed at least in sections on the carrier, of a material based on crosslinked gelatin that is resorbable under physiological conditions, wherein the adhesion between the carrier and the layer and/or between individual layers can be neutralised.

This removal of the adhesion promotes a separation of one or more layers from the stent according to the invention under physiological conditions. The physiological conditions, to which the vascular stent according to the invention is exposed during its use in the body of a human or animal, i.e. in particular the conditions prevailing in the blood, may be defined in this case by so-called physiological standard conditions and reconstructed in vitro. By physiological standard conditions in the context of the present invention is meant the incubation in PBS buffer (pH 7.2) at 37° C.

Preferably, one or more layers of the resorbable material are detachable individually. By the detachment of a layer in the sense of the present invention is meant an, at least in sections, two-dimensional separation of the resorbable material that forms the layer from the layer underneath or from the carrier. In other words, what occurs is a detachment of sections or fragments of the layer that still possess a certain structural integrity. This separation process is to be regarded as in contrast to a continuous degradation or resorption of the layer on a molecular level, whereby the layer is substantially fully resorbed before a detachment in the sense described above occurs.

The advantageous effect of the stent according to the invention is based on the fact that, by virtue of the neutralisation of the adhesion and the separation of one or more layers of the resorbable material from the vascular stent, cells, tissue or thrombi that have formed on the surface of the stent are also separated from the stent and removed by the blood stream from the relevant region of the vessel. Thus, this process leads to a cleaning of the stent and a renewal of its surface, thereby preventing or at least delaying restenosis without any need to use anti-proliferatives or similar active substances.

For the present invention the initially existing adhesion between the layer and the carrier and/or between the layers is important in order that by means of the controllable neutralisation of the adhesion the separation of two-dimensional layer parts is possible in a purposefully timed and predeterminable manner and the stent exhibits defined properties up to the start of the separation.

The possibility of neutralising the adhesion between individual layers that is provided according to the invention may be achieved by various measures. Firstly, adhesive layers of a material that is soluble under physiological conditions may be provided between individual layers of the resorbable material. For such adhesive layers various materials are conceivable, for example low-molecular, soluble collagen hydrolysate.

Preferred carriers have a microscopically smooth, closed surface. When the layers are applied to the carrier, this prevents material from depositing in pores, thereby resulting in an adhesion based on positive-locking effects. This applies in particular also in the case of the use of carriers in the form of small tubular lattice frames, which are also particularly suitable for the present invention. In the case of carriers having a lattice frame structure, the special advantage is achieved that during the two-dimensional separation of a layer no physiologically over-large and hence medically dangerous layer pieces are released into the blood circulation.

In the case of carriers having a lattice structure the preferred aim is a coating of the webs of the carrier, which in cross section are preferably completely surrounded by the layer and/or layers. Even after coating of the webs of the carrier, the spaces between the webs remain preferably open.

An expansion of the stent is then possible without threatening the integrity of the layer(s) on the carrier, i.e. the layer(s) on the webs of the carrier.

Furthermore, separating layers may also be provided between individual layers of the resorbable material, this being discussed in more detail further below.

The neutralisation of the adhesion between individual layers of the resorbable material (and/or between the carrier and the adjacent layer) may in particular also be based on an at least partial degradation of the material under physiological conditions, wherein by degradation is meant primarily those processes that ultimately lead also to resorption of the material. The degradation properties of the resorbable material may in this case be purposefully influenced by various measures, for example by the use of gelatins of differing molecular weights and/or by the admixture of further biopolymers to the gelatin-based material.

According to a preferred embodiment of the invention, the adhesion may be neutralised in dependence upon the degree of crosslinking of the gelatin. A higher degree of crosslinking of the gelatine leads to a slower degradation (and resorption) of the gelatin-based material, so that by means of this parameter the separation behaviour of individual layers may be adjusted in a simple manner.

In a particularly preferred manner the gelatin is crosslinked in such a way that the degree of crosslinking decreases within one or more layers of the resorbable material in the direction of the carrier. The effect achieved by a lower degree of crosslinking of the gelatin at the side of a layer facing the carrier is that in this region a faster degradation of the material occurs and hence the adhesion to the carrier (and/or to the layer underneath) is neutralised, while at the outside of the layer as a result of the higher degree of crosslinking of the gelatin a certain structural integrity is maintained and the previously described, at least in sections, two-dimensional separation of the layer is achieved.

The dimensionally stable material, from which the carrier is formed, is preferably a material that is inert under physiological conditions, in particular metal and/or plastics material. As carriers it is possible to use in particular expandable lattice frames or similar structures in the form of a small tube or hose.

The vascular stent according to the invention is used preferably in the cardiovascular area, and here in particular for the treatment of coronary vessels (coronary stent) because, here, vascular stenoses may lead to a cardiac infarction. The stent may however equally be used to treat stenoses in other areas of the body.

The effect according to the invention of at least reducing the risk of restenosis may already be achieved by arranging the layer(s) in sections on the carrier. It is however preferred if the at least one layer covers ca. 75% or more, in particular ca. 90% or more of the surface of the carrier. In a particularly preferred manner the at least one layer covers substantially the entire surface of the carrier.

The use according to the invention of gelatin as a base material for the layer(s) of resorbable material offers the advantage that gelatin is a substantially fully resorbable product that is tolerated extremely well by the body and may be manufactured in a reproducible purity and quality.

Within the framework of the present invention gelatin moreover has a particularly advantageous effect insofar as it promotes angiogenesis, i.e. the regeneration of blood vessels. Studies relating to this have shown that by introducing gelatin-containing shaped bodies into the body of a human or animal a local angiogenesis-promoting effect occurs. This applies not only to shaped bodies which are porous, where a growing of capillary vessels into the porous structure was observed (see German patent application 10 2005 054 937), but in particular also to shaped bodies which are non-porous, such as for example films, where the angiogenesis-promoting effect is observed in the area surrounding the shaped body.

It was discovered that the cause of the initially mentioned higher mortality with drug-coated stents lies primarily in an undesirable side effect of the anti-proliferative active substances used in the coated stents, namely a prevention of angiogenesis in the area surrounding the relevant vessel. In the event of stenosis, a natural reaction of the body is to bridge the occlusion by regenerating blood vessels. As this process is inhibited by anti-proliferatives or the like, in the event that restenosis nevertheless occurs no collateral blood vessels are available and the result is a cardiac infarction (P. Meier et al., Journal of American Cardiology 2007 (49) 15 to 20).

The possibility of dispensing with anti-proliferative active substances in the stent according to the invention means that not only is an angiogenesis-inhibiting effect avoided but, on the contrary, angiogenesis is stimulated by the gelatin-based material.

The vascular stent according to the invention therefore, on the one hand, reduces or delays the risk of restenosis as a result of the self-cleaning effect of the stent surface and, on the other hand, simultaneously promotes the generation of collateral blood vessels owing to the angiogenesis-promoting effect of the gelatin in the area surrounding the relevant vessel. Should restenosis nevertheless occur, in particular after all of the layers of the stent have separated, collateral blood vessels are available as a natural bypass system.

Dispensing with anti-proliferative agents moreover offers further advantages. For example, these active substances prevent not only the depositing of tissue, which may lead to restenosis, but also endothelialization of the stent. Endothelialization produces around the stent a layer of connective tissue that is compatible with the components of the blood, thereby preventing the activation of blood platelets and clotting factors on the stent material, i.e. this process counteracts a thrombosis in the region of the stent.

The resorbable material according to the invention is preferably formed predominantly by crosslinked gelatin. This means that the gelatine represents the largest fraction compared to any further components of the material that are used.

Particularly suitable types of gelatin are pork-rind gelatin, which is preferably high-molecular and has a Bloom value of ca. 160 to 320 g.

In order to guarantee an optimum biocompatibility of the stent according to the invention, as a starting material preferably a gelatin having a particularly low endotoxin content is used. Endotoxins are metabolic products or fragments of microorganisms that occur in the raw animal material. The endotoxin content of gelatin is indicated in international units per gram (I.U./g) and determined in accordance with the LAL test, the performance of which is described in the fourth edition of the European Pharmacopoeia (Ph. Eur. 4).

In order to keep the endotoxin content as low as possible, it is advantageous to destroy the microorganisms as early as possible in the course of gelatin production. Furthermore, appropriate hygiene standards should be observed during the production process.

The endotoxin content of gelatin may therefore be drastically reduced by specific measures during the production process. These measures primarily include the use of fresh raw materials (for example pork rind) avoiding periods of storage, careful cleaning of the entire production plant immediately before the start of gelatin production and optionally the replacement of ion exchangers and filter systems in the production plant.

The gelatin used within the framework of the present invention preferably has an endotoxin content of ca. 1,200 I.U./g or less, even more preferably of ca. 200 I.U./g or less. Optimally the endotoxin content is ca. 50 I.U./g or less, determined in each case in accordance with the LAL test. Compared to this, many commercially available gelatins have endotoxin contents of more than 20,000 I.U./g.

By means of the crosslinking according to the invention of the as such soluble gelatin, the gelatin is converted to an insoluble material that is however resorbable under physiological conditions. In this case, the rate of resorption and/or degradation of the material is dependent upon the degree of crosslinking of the gelatin and may be adjusted over a relatively wide range, as has already been mentioned above. In particular, the point in time of the detachment of individual layers may be preselected by means of the respective degree of crosslinking of the gelatin.

Shaped bodies based on crosslinked gelatin, the resorption properties and the manufacture thereof are described in the published patent application DE 10 2004 024 635 A1.

The crosslinking of the gelatin may be effected both by chemical and by enzymatic crosslinking agents. Of the chemical crosslinking agents a crosslinking using formaldehyde is preferred, which simultaneously effects sterilization.

A preferred enzymatic crosslinking agent is the enzyme transglutaminase.

A suitable procedure for the manufacture of shaped bodies based on crosslinked gelatin is a two-stage crosslinking process, whereby in a first stage the gelatin is partially crosslinked in solution. From the partially crosslinked gelatin solution a shaped body is then manufactured and subjected to a second crosslinking step.

The second crosslinking step may be carried out in particular by the action of a crosslinking agent in the gas phase, preferably formaldehyde.

In accordance with this method the vascular stent according to the invention may be manufactured by applying a partially crosslinked solution of the gelatin-based material onto the surface of the carrier, for example by dipping the carrier into the solution. After drying of the solution, a carrier having a layer of the resorbable material is obtained, which is then subjected to the second crosslinking step, for example with formaldehyde in the gas phase.

This second crosslinking step is a simple way of obtaining the preferred gradient in the degree of crosslinking because the crosslinking agent is able to penetrate into the layer only from the outside of the layer, this leading to a higher degree of crosslinking at the outside and a lower degree of crosslinking at the inner side facing the carrier.

Within the framework of the invention it is equally conceivable to provide no crosslinking of the gelatin in the solution but only a single crosslinking step after applying the layer onto the carrier.

The resorbable material preferably contains one or more softening agents. This increases the flexibility of the material, which may be advantageous particularly with regard to the expansion of the stent after implantation. An adequate flexibility makes it possible extensively to prevent the at least one layer from becoming damaged or from mechanically separating from the carrier during expansion of the stent.

Preferred softening agents are for example glycerine, oligoglycerines, oligoglycols, sorbitol and mannitol. The softening agent content in the resorbable material is preferably ca. 12 to ca. 40 wt. %, more preferably ca. 16 to ca. 25 wt. %.

According to a preferred embodiment of the invention, a plurality of layers of the resorbable material are disposed on the carrier. By providing a plurality of layers, which detach preferably in each case individually, the surface of the stent according to the invention may be repeatedly freed of deposits and so the period, during which the risk of restenosis is reduced, can be markedly prolonged. The vascular stent preferably comprises two to five layers of the resorbable material.

Stents according to the invention having a plurality of layers are relatively easy to manufacture by carrying out the previously outlined method steps (applying the optionally partially crosslinked gelatin solution, drying and second crosslinking) a number of times in succession.

The degree of crosslinking of the gelatin within each layer preferably decreases in the direction of the carrier. This promotes the neutralisation of the adhesion for the separation of each individual layer.

The individual layers of the resorbable material are advantageously detachable successively from the outside in. Such a successive detachment is already promoted by the fact that the layers situated further in are protected to a certain extent from degradation in each case by the layers situated above. This applies even if all of the layers have the same average degree of crosslinking of the gelatin.

It is however preferred if the average degree of crosslinking of the individual layers increases in the direction of the layer adjacent to the carrier. By means of a high degree of crosslinking of the inner layers, the degradation and detachment of these layers may be additionally delayed. Furthermore, the separation behaviour of the individual layers may be purposefully adapted to the respective requirements, i.e. in particular to the anticipated intensity of deposits and/or tissue formation on the stent. Ideally, the period up to detachment of the innermost layer is long enough to allow collateral blood vessels to be generated, promoted by the angiogenesis-promoting effect of the gelatin-based material, before this detachment occurs.

The average degrees of crosslinking of the individual layers may be selected for example in such a way that the outermost layer detaches after ca. 1 to 2 weeks and the innermost layer adjacent to the carrier detaches after ca. 3 to 6 months. The specified periods refer to the time, at which the stent according to the invention is exposed to physiological conditions, i.e. is in particular inserted into a blood vessel.

Different degrees of crosslinking of the individual layers may be realized in the previously described manufacturing method by different concentrations of crosslinking agent in the gelatin solution and/or by different concentrations or reaction times of the crosslinking agent in the second crosslinking step.

The thickness of the individual layers of the resorbable material is preferably in the region of ca. 5 to ca. 50 µm.

According to a further embodiment of the invention, one or more separating layers are disposed between a plurality of layers of the resorbable material and/or at the outside of the layer(s). By means of such separating layers various advantageous effects may be achieved.

First of all, the adhesion between a plurality of layers may be reduced by means of the separating layers. With progressive degradation of the gelatin-based material in the respective outermost layer, the neutralisation of the adhesion and the separation of this layer is accelerated by means of the separating layer, wherein the separating layer itself remains on the outside of the layer situated underneath.

A resorbable material is preferably used for the separating layers. This material preferably has a longer resorption time than the gelatin-based material in the at least one layer, so that the separating layer is still present on the outside of a layer at the time of the detachment of this layer.

The separating layers may be formed for example by a releasing wax.

A further effect that may be achieved by means of a separating layer disposed on the respective outermost layer is that the deposit of cells or tissue on the surface of the stent is reduced by virtue of the separating layer having an adhesion-inhibiting effect with regard to these deposits. This additionally counteracts the risk of restenosis. If the extent of the deposits is reduced, a later time of detachment of the layer(s) of the resorbable material may also be selected.

The at least one separating layer preferably contains modified gelatin. It has been found that by means of a chemical modification of gelatin an adhesion-inhibiting effect with regard to cells may be achieved.

According to a further embodiment of the invention, it is provided that the modified gelatin is contained in one or more layers of the gelatin-based material. In this way, an effect comparable to that in the case of separating layers of modified gelatin may be achieved.

While separating layers may be formed to a large extent or substantially entirely by modified gelatin, the possible content of modified gelatin in the layers is limited insofar as adverse effects on the crosslinkability of the gelatin and on the degradation behaviour should be avoided.

The modified gelatin is preferably a gelatin modified with fatty acid groups. One example of this is the modification of gelatin with dodecenylsuccinate.

The modification is effected here in particular at the free amino groups of the lysine groups of the gelatin. Preferably ca. 10 to ca. 80% of the lysine groups of the modified gelatin are modified with fatty acid groups.

A further possible way of achieving an adhesion-inhibiting effect is an anionic modification of the gelatin, for example the succination of side chains.

BRIEF DESCRIPTION OF THE SEVERAL VIEWS OF THE DRAWINGS

These and further advantages of the invention are described in detail by way of the following examples and with reference to the drawings. The drawings specifically show.

DETAILED DESCRIPTION OF THE INVENTION

Figure 1:
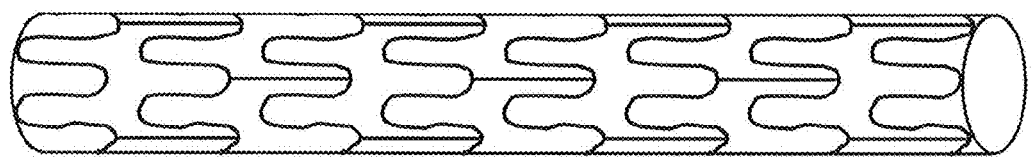
FIG. 1: representation of a stent according to the invention in a compressed state prior to implantation.
Figure 2:
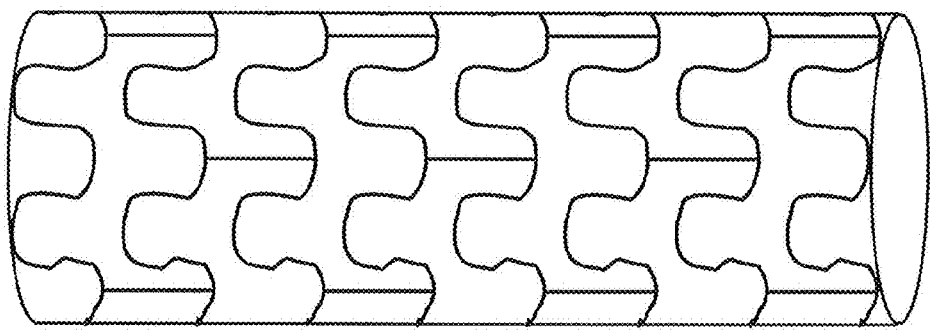
FIG. 2: representation of a stent according to the invention in an expanded state after implantation.

FIGS. 1 and 2 show an embodiment of a vascular stent according to the invention, which is used in particular as a coronary stent. The stent comprises a carrier in the form of a small tubular lattice frame made of metal or plastics material, on the surface of which a plurality of layers of a resorbable material based on crosslinked gelatin are disposed.

FIG. 1 shows the stent in a compressed state. The stent in this state has only a relatively small cross section and may therefore be introduced into a vascular region affected by stenosis.

After being implanted, the stent is widened for example by means of a balloon catheter, i.e. is expanded radially so that the affected vessel is wide open and supported by the stent. This expanded state of the stent is shown in FIG. 2. Both the lattice frame of the carrier and the layers of resorbable material are flexible enough to allow this expansion process to occur.

Figure 3:
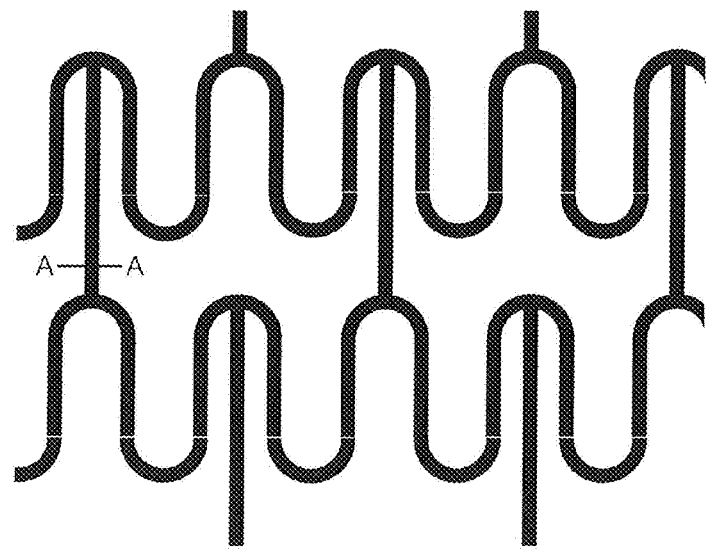
FIG. 3: representation of a detail of the structure of a stent according to the invention.

FIG. 3 shows an enlarged detail of the frame structure of the stent according to the invention. The lattice frame of the carrier is formed by a plurality of interconnected webs, wherein the layers are disposed on the surface of these webs. Preferably, in the present case as large a proportion as possible of the total surface of the carrier is covered.

The geometry of the lattice structure and/or the arrangement of the webs that is shown in FIG. 3 is in the present case merely by way of example. The lattice structure should however be so designed that by bending or deforming the webs an expansion of the stent is possible.

Figure 4:
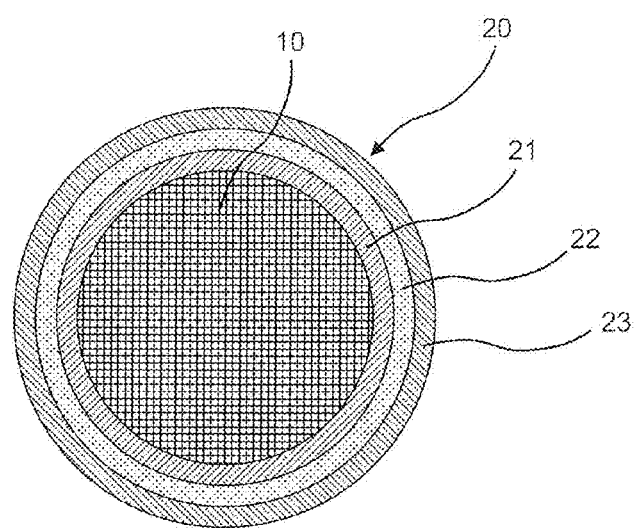
FIG. 4: schematic cross-sectional representation of the layers of a stent according to the invention.

A schematic representation of the cross section through a web 10 of the carrier, for example along the line A-A, is shown in FIG. 4. The web, which for example has a diameter in the region of 100 to 200 µm, is surrounded by three layers, namely an inner layer 21 adjacent to the web 10, a middle layer 22 and an outer layer 23. As an alternative to this embodiment, one, two or more than three layers may be provided.

All of the layers are formed by a material based on crosslinked gelatin that is resorbable under physiological conditions. To increase the flexibility of the layers, the material may additionally comprise a softening agent, for example glycerine.

The degree of crosslinking of the gelatin preferably decreases within each of the three layers 21, 22 and 23 in the direction of the web 10 of the carrier. This means that for example the outer layer 23 has a lower degree of crosslinking at its inner side, i.e. the side facing the middle layer 22, than at its outer side 20.

This gradual degree of crosslinking leads under physiological conditions to a faster degradation of the gelatin-based material at the inside of the layer 23 and hence, after a preselected time, to a neutralisation of the adhesion to the layer 22 and to an, at least in sections, two-dimensional separation of the layer 23 from the layer 22. At the same time, deposits of cells or tissue that have formed on the outer side 20 of the layer 23, i.e. on the surface of the stent, are removed from the associated vascular region by the blood stream. After this separation, the layer 22 forms the outer layer, so that the process just described may be repeated with this layer.

The average degree of crosslinking of the gelatin in the individual layers 21, 22 and 23 preferably increases in the direction of the web 10, i.e. the layer 23 has the lowest and the layer 21 the highest average degree of crosslinking.

For example, the degrees of crosslinking in the individual layers are selected such that the layer 23 detaches ca. one to two weeks, the layer 22 ca. four to eight weeks and the layer 21 ca. three to six months after introduction of the vascular stent into a blood vessel.

The individual layers 21, 22 and 23 preferably have a thickness in the region of ca. 5 to ca. 50 µm.

Separating layers may be disposed between the individual layers 21, 22 and 23 and/or on the outer side 20 of the layer 23. Such separating layers may, on the one hand, accelerate the neutralisation of the adhesion between the individual layers and/or counteract the adhesion of cells and tissue.

The separating layers and/or the layers 21, 22 and 23 may in particular contain modified gelatin. In this way, the cell adhesion with regard to non-modified gelatin may be reduced, as is demonstrated in the following Example 1.

Example 1

Inhibition of Cell Adhesion by Modified Gelatin

The amino groups of the lysine groups in the gelatin may be converted to a succinated form by means of succinic acid anhydride, with the result that the $pK_S$ value of the gelatin material of 8 to 9, as is found for the unmodified gelatin, is lowered to ca. 4.

A further possible way of modifying the gelatin is to convert the amino groups of the lysine groups to dodecenyl-succinyl groups. The $pK_S$ value in this case is reduced to ca. 5 and at the same time a slight hydrophobing of the gelatin by the fatty acid group occurs.

In both cases, the cell adhesion with regard to a gelatin treated in this way decreases markedly, which is demonstrated in the tests described below using the example of porcine chondrocytes.

The degree of conversion of the lysine groups of the modified gelatin is preferably 30% or more. In the case of the dodecenyl-succinated gelatin degrees of conversion of 40 to 50% are often eminently sufficient, whereas in the case of the succinated gelatin an 80% to almost total conversion of the lysine groups produces the best results.

Figure 5:
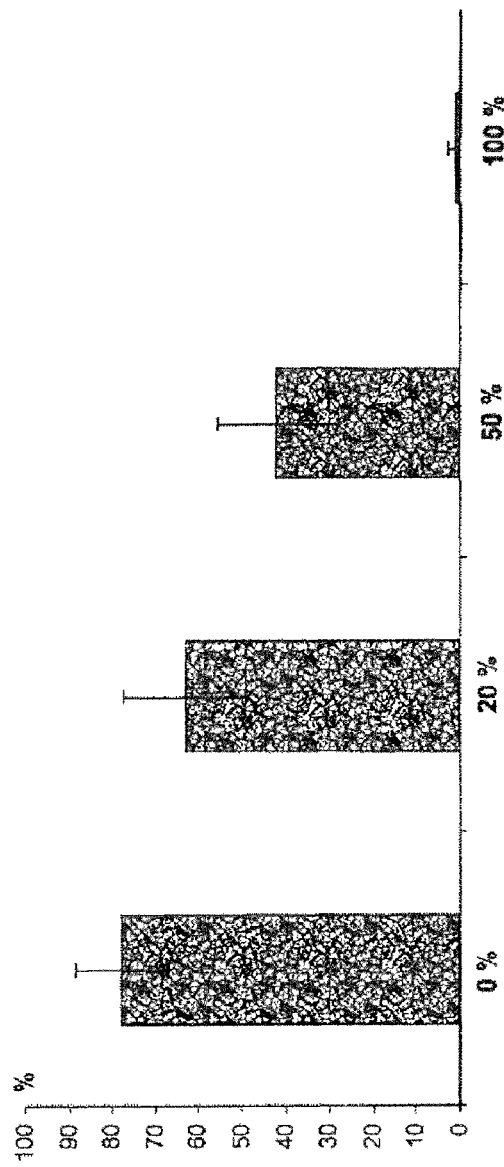
FIGS. 5 and 6: graphs relating to the adhesion-inhibiting effect of modified gelatin.
Figure 6:
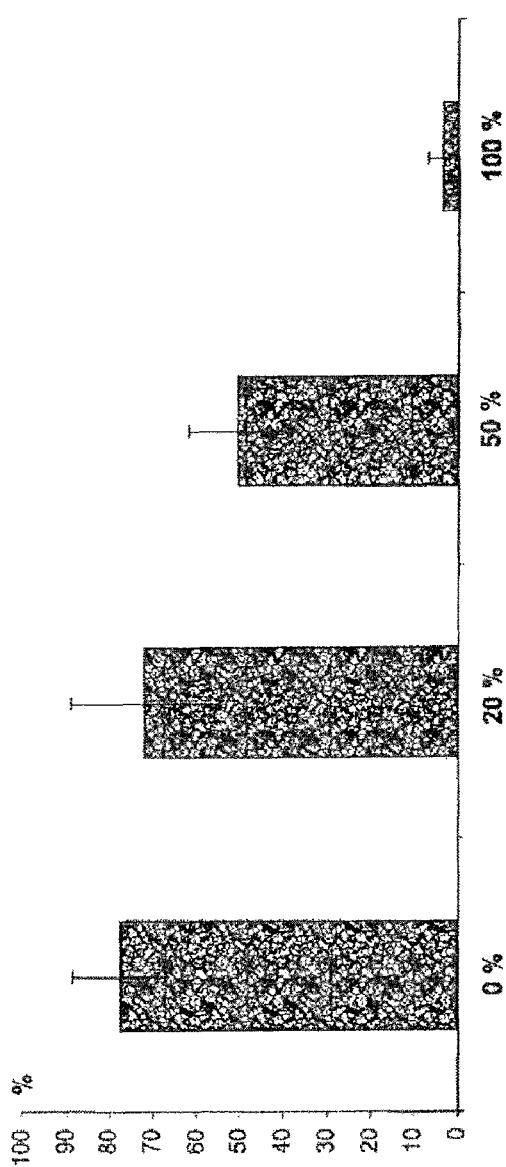

FIGS. 5 and 6 show cell adhesion results for test areas, applied for test purposes onto glass surfaces, of gelatin materials that were manufactured from pork-rind gelatin (MW 119 kDa) and a gelatin ca. 95% succinated at the lysine groups (FIG. 5) and ca. 45% dodecenyl-succinated gelatin (FIG. 6), respectively, of an identical type. In each case mixtures of unmodified gelatin with modified gelatin in the ratios 100:0, 80:20, 50:50 and 0:100 were tested.

In the tests in each case 20,000 porcine chondrocytes were incubated on a test area for 4 hours at 37° C. The excess was removed, the surface washed and the cells remaining on the surface fixed for subsequent analysis under a light-microscope. Comparable results were obtained with human chondrocytes.

The percentages indicated in the graphs represent the proportion of cells found on the film test areas compared to the number used for incubation, after the previously described procedure was carried out.

For both types of modified gelatin, population effects close to zero were obtained in the case of exclusive use of modified gelatin.

This marked inhibition of the cell adhesion by chemically modified gelatin may be utilized within the framework of the present invention to reduce the deposit of cells and tissue on the respective outer layer of the stent.

The separating layers preferably disposed between the individual layers may in this case contain a very high proportion of modified gelatin of up to 100%. As these separating layers, after detachment of the layer situated above, form in each case the surface of the stent, a very strong adhesion-inhibiting effect of the stent according to the invention may therefore be achieved.

Example 2

Promotion of Angiogenesis

The following example is intended to demonstrate the local angiogenesis-promoting effect of gelatin-based materials.
Manufacture of Films from a Gelatin-Based Material Gelatin films having three different degrees of cross-linking (films A, B and C) were manufactured by means of a two-stage crosslinking process.

For each of the three batches 25 g of pork-rind gelatin (300 g Bloom), 9 g of an 85 wt. % glycerine solution and 66 g of distilled water were mixed and the gelatin was dissolved at a temperature of 60° C. After ultrasonic degassing of the solutions, for carrying out the first crosslinking step an aqueous formaldehyde solution (2.0 wt. %, room temperature) was added, namely 3.75 g of this solution to batch A and 6.25 g of the solution to each of the batches B and C.

The mixtures were homogenized and applied at ca. 60° C. with a doctor blade in a thickness of ca. 250 μm onto a polyethylene support.

After drying at 30° C. and a relative atmospheric humidity of 30% for approximately one day, the films were removed from the PE support and further dried for ca. 12 hours under the same conditions. For carrying out the second crosslinking step, the dried films (thickness ca. 50 μm) were exposed in a desiccator to the equilibrium vapour pressure of a 17 wt. % aqueous formaldehyde solution at room temperature. In the case of films A and B the time of exposure to the formaldehyde vapour was 2 hours, in the case of film C 17 hours.

Of the formed bodies thus produced, film A on the whole has the lowest degree of crosslinking and film C on the whole the highest degree of crosslinking, with film B lying in between. This is reflected in the different degradation behaviour of the films, wherein the resorption times of the described films under physiological conditions in the animal experiment (see below) are between ca. 14 days (film A) and ca. 21 days (film C).
Confirmation of the Angiogenesis-Promoting Effect in the Animal Experiment The angiogenesis-promoting effect of the gelatin films A, B and C in vivo was investigated in the animal experiment. As test animals, 10-week old mice of the strain Balb/C of the company Charles River (Sulzfeld) and having a body weight of 20 g were used.

As substrates, 5×5 mm² pieces of the previously described gelatin films were used in each case. In each case two film pieces of a specific degree of cross-linking were implanted in the mice subcutaneously in the region of the back of the neck. For this purpose, the animals were anaesthetized and the fur at the back of the neck was shaved off. Using forceps a piece of the neck skin was lifted and a ca. 1 cm long incision was made. Through this incision blunt forceps were used to create a subcutaneous pocket, into which two each of the film pieces were inserted using forceps. The wound was closed by means of two single-button sutures.

After 12 days the animals were killed and the angiogenetic effect of the implanted substrates was evaluated visually.

Figure 7:
FIG. 7: photographic representation of the generation of blood vessels in the subcutaneous tissue of a mouse.

FIG. 7 shows as a negative control the corresponding region of the subcutaneous tissue of a mouse, in which no implantation of the angiogenesis-promoting substrate was carried out. Only a relatively slight interspersion with blood vessels is to be observed, as is normal for the subcutaneous skin tissue of the mouse.

Figure 8A:
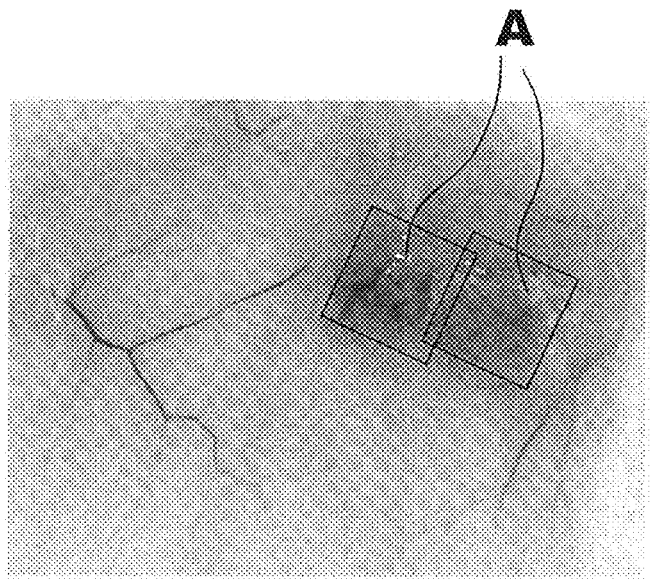
FIGS. 8a to c: photographic representations of the increased generation of blood vessels in the presence of various angiogenesis-promoting substrates based on crosslinked gelatin.
Figure 8B:
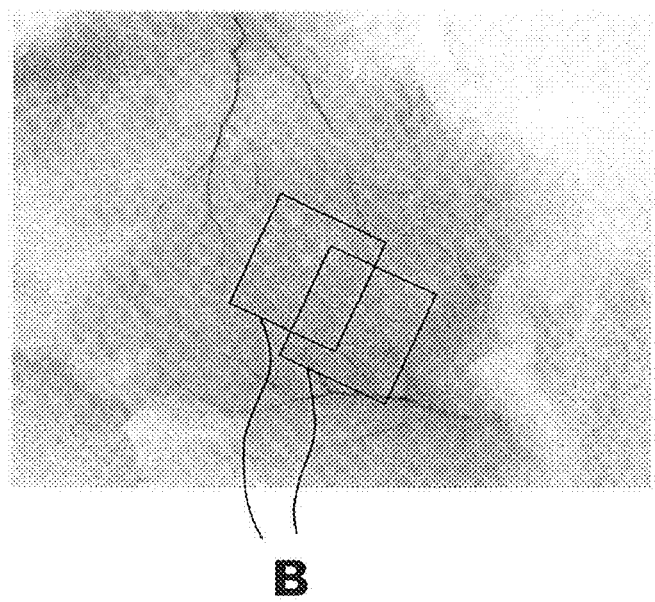
Figure 8C:
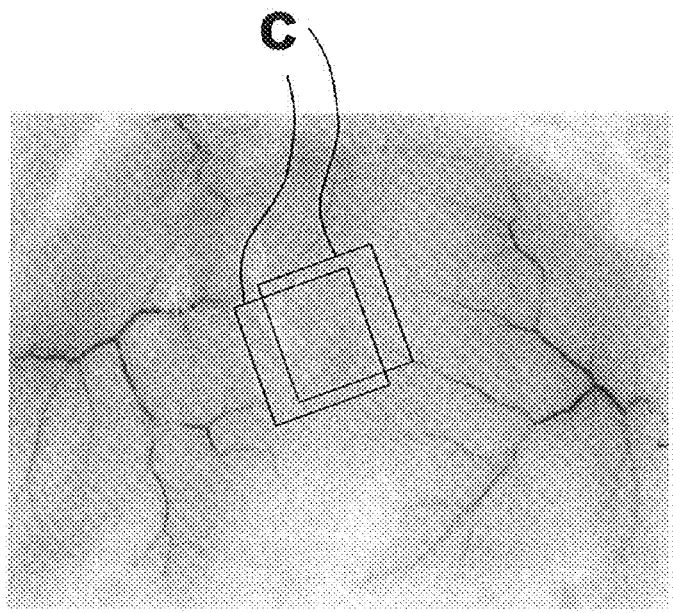

FIGS. 8a to 8c show photographs of the subcutaneous skin tissue in the region of the implanted film pieces A, B and C after the corresponding mice were killed 12 days after implantation. The position of the film pieces is marked by black squares (reference character A, B or C for the corresponding film), as the films themselves are hard to see in the photographs. By way of experiment some of the films were dyed with Coomassie Brilliant Blue, as may be seen in FIG. 8a.

All three images reveal a markedly increased generation of blood vessels in the area surrounding the implanted film pieces. Both the number and the size of the blood vessels are markedly greater than in the negative control in FIG. 7. This result proves that angiogenesis may be locally stimulated by means of a material based on crosslinked gelatin that is resorbable under physiological conditions.

This local angiogenesis-promoting effect of materials based on crosslinked gelatin leads, in the vascular stent according to the invention, to a particularly advantageous effect. The layers of gelatin-containing material stimulate the generation of collateral blood vessels in the region of the vessel treated with the stent, so that in the event of restenosis, for example after the complete detachment of all of the layers, the risk of a cardiac infarction may be markedly reduced.

Example 3

Time-Dependent Separation Behaviour of a Plurality of Layers of a Gelatin-Based Material In order to enable qualitative and quantitative determination of the time-dependent separation behaviour of a plurality of layers of a material based on crosslinked gelatin, the test described below was carried out.

In order to facilitate visual evaluation, the carrier used here was not a lattice frame of a stent but a flat polyethylene support, onto which two layers of the resorbable material were applied over a large area. Resorbable materials of the same composition may be applied within the framework of the present invention onto the surface of a carrier of a vascular stent according to the invention.

In order to be able to see the difference between the two layers of the resorbable material in the test, the first layer was dyed with a white pigment (titanium dioxide) and the second layer with a red food dye (Candurin Wine Red). For the same reason, layers of a greater thickness than the thicknesses preferred within the framework of the stent according to the invention were manufactured.

A first test batch 3-1 was carried out as follows:
20 g of pork-rind gelatin (300 g Bloom), 8 g of glycerine, 1 g of titanium dioxide and 69 g of distilled water were mixed and the gelatin was steeped for 30 minutes at room temperature. Then the gelatin was dissolved by heating the mixture to 60° C. and the solution was homogenized and ultrasonically degassed.

This gelatin solution was applied by a doctor blade in a thickness of ca. 550 μm onto a flat polyethylene carrier in order to form the first layer of resorbable material on the carrier.

For carrying out a crosslinking of the gelatin, the polyethylene carrier having the first layer was exposed in the desiccator to the equilibrium vapour pressure of a 10 wt. % aqueous formaldehyde solution for 17 hours at room temperature.

Because the formaldehyde vapour is able to penetrate into the layer of resorbable material substantially only from the side remote from the carrier, a degree of crosslinking of the gelatin that decreases in the direction of the carrier is obtained by this method.

The first layer of the gelatin-based material was then dried overnight at 26° C. and a relative atmospheric humidity of 10%. The dried layer had a thickness of ca. 100 μm.

The carrier having the crosslinked first layer was cooled to ca. 4° C. To produce a separating layer, a Boeson releasing wax was sprayed onto the layer and spread evenly using a soft cloth.

The gelatin solution for the second layer of resorbable material was manufactured in the same way as the solution for the first layer, wherein 20 g of gelatin, 4 g of glycerine, 73 g of distilled water and, instead of titanium dioxide, 1 g of Candurin Wine Red were used as starting materials.

The resulting gelatin solution was applied likewise in a thickness of ca. 550 μm onto the first layer of resorbable material provided with the releasing wax.

The second layer was subjected likewise to crosslinking with formaldehyde vapour, as described for the first layer, only with the difference that the time of exposure to the crosslinking agent was only 2 hours instead of 17 hours. Consequently, the second layer has a lower average degree of crosslinking than the first layer, wherein the degree of crosslinking of the gelatin decreases within the second layer likewise in the direction of the carrier.

Drying was effected in the manner described for the first layer. After drying, the second layer had a thickness of ca. 70 μm.

The time-dependent separation behaviour of the two layers of gelatin-based material under physiological conditions was determined by incubation in PBS buffer (pH 7.2) at 37° C. By means of these physiological standard conditions it is possible to reconstruct the conditions such as prevail during use of the vascular stent according to the invention in the body.

Figure 9:
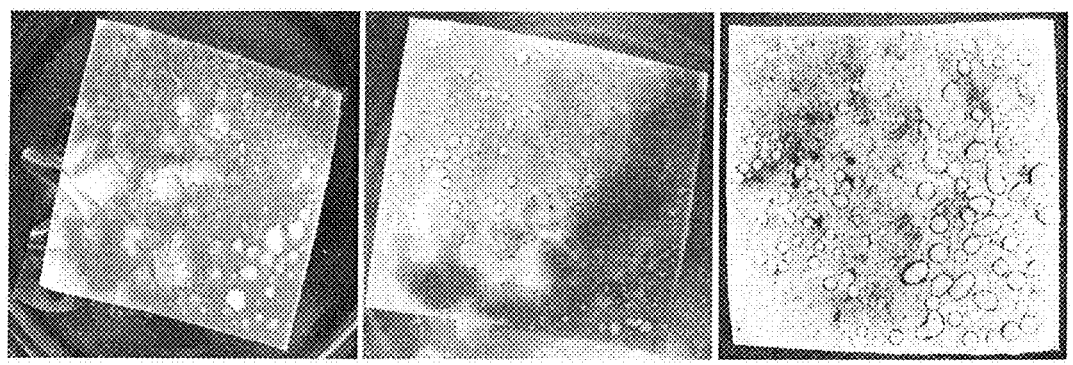
FIG. 9: photographic representation of the time-dependent separation behaviour of two layers of a gelatin-based material.
Figure 9:
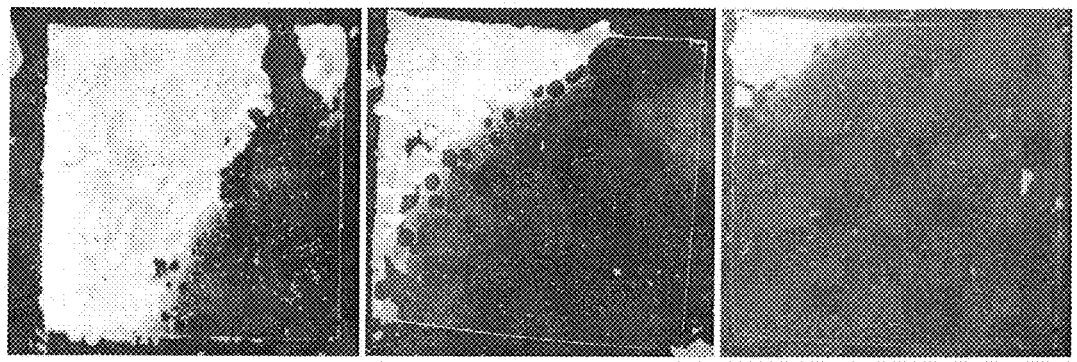

FIG. 9 shows photographs of the carrier having the two layers according to the test batch 3-1 after 5, 6, 7, 10, 11 and 12 days of incubation in the PBS buffer.

As may be seen in the top three photographs, between the $5^{th}$ and $7^{th}$ day of incubation the neutralisation of the adhesion of the second (outer) layer and the separation of this layer from the first layer situated underneath occurs. The originally red-dyed second layer appears in the top three photographs of FIG. 9 as a dark area, while the white-dyed first layer is visible as a markedly lighter area. After 5 days ca. 20% of the second layer has separated and individual white specks of the first layer are visible. After 6 days ca. 65% of the second layer has separated, the second layer being present substantially only in the bottom right area of the carrier. After 7 days of incubation the second layer has finally substantially completely separated. Over the entire area of the test batch the first layer is now visible, wherein this layer is in part already swollen and blistering but is substantially still intact.

The separation of the first layer of gelatin-based material from the carrier occurs substantially between the $10^{th}$ and $12^{th}$ day of incubation, as may be seen in the bottom three photographs of FIG. 9. In the course of separation of the first layer (white area) the polyethylene carrier becomes visible as a dark background. After 10 days of incubation ca. 35%, after 11 days ca. 80% and after 12 days ca. 95% of the first layer has separated from the carrier.

The described result demonstrates that with a plurality of layers of a resorbable material based on crosslinked gelatin it is possible by means of different average degrees of crosslinking in the individual layers to achieve control of the separation behaviour to the effect that the in each case outer layer has substantially completely separated before separation of the layer underneath begins. By virtue of this effect it is possible in the case of the vascular stent according to the invention to achieve a repeated renewal of the stent surface as a result of the successive separation of a plurality of layers of a resorbable material.

The test also further demonstrates that by neutralising the adhesion between the layers of the gelatin-based material an, at least in sections, two-dimensional separation of a layer from the layer below or from the carrier occurs. This is promoted by a lower degree of crosslinking of the gelatin at the inside of the respective layer.

A second test batch 3-2 was carried out in the same way as the previously described test batch 3-1, with the difference that the separating layer (Boeson releasing wax) between the two layers of the gelatin-based material was dispensed with. In this batch the first layer had a thickness of ca. 80 μm and the second layer a thickness of ca. 100 μm.

In the test batch 3-2 too, a sequential separation behaviour of the two layers was observed. However, in this case ca. 20% of the first layer had separated after 6 days of incubation, ca. 55% after 7 days of incubation and almost 100% only after 10 days of incubation.

The second layer of the batch 3-2 was still substantially intact after 13 days. After 18 days ca. 20% and after 25 days ca. 70% of the second layer had separated.

This result demonstrates in particular that through the use of separating layers the separation of individual layers from the layer below, given an identical degree of crosslinking of the gelatin, may be accelerated (second layer of batch 3-1 compared to batch 3-2). The later separation of the first layer of batch 3-2 may be ascribed to its having a greater thickness and being shielded by the separating layer.

A further test batch 3-3 was carried out in the same way as batch 3-2, with the difference that 2 ml of a 1 wt. % aqueous formaldehyde solution was added in each case to the gelatin solutions for the first and second layer prior to application by a doctor blade. As a result of this two-stage crosslinking both layers of this batch have a higher average degree of crosslinking compared to the batches 3-1 and 3-2. This led to a, once again, later separating time of the first layer of this batch, of which layer only less than ca. 5% had separated from the carrier after 25 days of incubation. Complete separation occurred only after 32 days.

The invention claimed is:

1. A vascular stent, comprising a carrier of a dimensionally stable material, as well as a plurality of layers, which are disposed at least in sections on the carrier, of a material comprising crosslinked gelatin that is resorbable under physiological conditions, wherein the average degree of crosslinking of the gelatin in the individual layers increases in the direction of the layer adjacent to the carrier, and wherein the layers are detachable individually.

2. The vascular stent according to claim 1, wherein adhesive layers of a material that is soluble under physiological conditions are disposed between individual layers of the resorbable material.

3. The vascular stent according to claim 1, wherein the degree of crosslinking of the gelatin decreases within one or more layers in the direction of the carrier.

4. The vascular stent according to claim 1, wherein the carrier is formed from metal and/or from plastics material.

5. The vascular stent according to claim 1, wherein the layers cover about 75% or more of the surface of the carrier.

6. The vascular stent according to claim 5, wherein the layers cover about 90% or more of the surface of the carrier.

7. The vascular stent according to claim 6, wherein the layers cover substantially the entire surface of the carrier.

8. The vascular stent according to claim 1, wherein the material comprising crosslinked gelatin has an angiogenesis-promoting effect.

9. The vascular stent according to claim 1, wherein the resorbable material is formed predominantly of crosslinked gelatin.

10. The vascular stent according to claim 1, wherein the gelatin has a Bloom value in the region of about 160 to about 320 g.

11. The vascular stent according to claim 1, wherein the gelatin has an endotoxin content of about 1,200 I.U./g or less, that is determined in accordance with the LAL test.

12. The vascular stent according to claim 1, wherein the gelatin is crosslinked using formaldehyde.

13. The vascular stent according to claim 1, wherein the gelatin is crosslinked using transglutaminase.

14. The vascular stent according to claim 1, wherein the resorbable material contains one or more softening agents.

15. The vascular stent according to claim 1, wherein the vascular stent comprises two to five layers of the resorbable material.

16. The vascular stent according to claim 1, wherein the degree of crosslinking of the gelatin decreases within each layer in the direction of the carrier.

17. The vascular stent according to claim 1, wherein the individual layers of the resorbable material are detachable successively from the outside in.

18. The vascular stent according to claim 1, wherein the thickness of the layers is about 5 to about 50 μm.

19. The vascular stent according to claim 1, wherein one or more separating layers are disposed between a plurality of layers of the resorbable material and/or on the outer side of the layer(s).

20. The vascular stent according to claim 19, wherein one or more separating layers have a longer resorption time than the layers of the material comprising crosslinked gelatin.

21. The vascular stent according to claim 19, wherein the one or more separating layers contain modified gelatin.

22. The vascular stent according to claim 21, wherein the modified gelatin is a gelatin modified with fatty acid groups.

23. The vascular stent according to claim 22, wherein the modified gelatin comprises lysine groups and wherein about 10% to about 80% of the lysine groups of the modified gelatin are modified with fatty acid groups.

24. The vascular stent according to claim 1, wherein one or more layers contain modified gelatin.

* * * * *